(12) United States Patent
Van Gompel et al.

(10) Patent No.: US 8,388,595 B2
(45) Date of Patent: Mar. 5, 2013

(54) DISPOSABLE UNDERGARMENT WITH A DETACHABLE CROTCH MEMBER AND METHOD FOR THE USE THEREOF

(75) Inventors: Paul T. Van Gompel, Hortonville, WI (US); Russell E. Thorson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1745 days.

(21) Appl. No.: 10/325,481

(22) Filed: Dec. 19, 2002

(65) Prior Publication Data
US 2004/0122401 A1 Jun. 24, 2004

(51) Int. Cl.
*A61F 13/15* (2006.01)
*A61F 13/20* (2006.01)

(52) U.S. Cl. .................................. 604/391; 604/386

(58) Field of Classification Search .......... 604/358–402; 450/103
See application file for complete search history.

(56) References Cited

U.S. PATENT DOCUMENTS

| | | | |
|---|---|---|---|
| 1,830,528 A * | 11/1931 | Cohon | ......................... 450/103 |
| 1,833,960 A | 12/1931 | Alsop | |
| 2,004,088 A | 6/1935 | Alsop | |
| 3,672,371 A | 6/1972 | Roeder | |
| 3,776,233 A | 12/1973 | Schaar | |
| 3,943,930 A | 3/1976 | Schaar | |
| 3,981,306 A | 9/1976 | Krusko | |
| 3,995,638 A | 12/1976 | Schaar | |
| 3,999,548 A | 12/1976 | Hernandez | |
| 4,280,230 A | 7/1981 | LaFleur | |
| 4,698,855 A * | 10/1987 | Hicks | ............................. 2/402 |
| 4,731,070 A | 3/1988 | Koci | |
| 4,747,846 A * | 5/1988 | Boland et al. | ............ 604/385.22 |
| 4,753,645 A | 6/1988 | Johnson | |
| 4,834,736 A * | 5/1989 | Boland et al. | ............ 604/385.22 |
| 4,883,481 A * | 11/1989 | Blanchard | ............... 604/385.11 |
| 4,892,536 A | 1/1990 | DesMarais et al. | |
| 4,917,697 A | 4/1990 | Osborn, III et al. | |
| 5,062,840 A | 11/1991 | Holt et al. | |
| 5,187,817 A | 2/1993 | Zolner | |
| 5,389,095 A * | 2/1995 | Suzuki et al. | ............ 604/385.22 |

(Continued)

FOREIGN PATENT DOCUMENTS

| | | |
|---|---|---|
| EP | 0 815 821 A | 1/1998 |
| EP | 0907510 B1 | 3/2002 |

(Continued)

OTHER PUBLICATIONS

International Search Report in corresponding International Application No. PCT/US03/28638, dated Feb. 12, 2004, 8 pages.

*Primary Examiner* — Melanie Hand
(74) *Attorney, Agent, or Firm* — R. Joseph Foster, III

(57) ABSTRACT

A disposable undergarment includes a body chassis member elongatable in at least a first direction between at least a first condition and second condition. The body chassis member has a greater elongation when in the second condition than when in the first condition. The disposable undergarment further includes a crotch member detachably connected to the body chassis member at at least one attachment location. At least a portion of the at least one attachment location is detached as the body chassis member is elongated between the first and second conditions. In one preferred embodiment, the crotch member includes an absorbent component. Methods of using the undergarment and of instructing a user about the use of the garment are also provided.

36 Claims, 5 Drawing Sheets

U.S. PATENT DOCUMENTS

| | | | |
|---|---|---|---|
| 5,527,303 A | 6/1996 | Milby, Jr. et al. | |
| 5,575,785 A | 11/1996 | Gryskiewicz et al. | |
| 5,593,400 A | 1/1997 | O'Leary | |
| 5,653,842 A | 8/1997 | Kuen | |
| 5,658,269 A | 8/1997 | Osborn, III et al. | |
| 5,772,649 A * | 6/1998 | Siudzinski | 604/386 |
| 5,846,232 A * | 12/1998 | Serbiak et al. | 604/385.29 |
| 5,885,264 A * | 3/1999 | Matsushita | 604/361 |
| 5,891,124 A | 4/1999 | Nomura et al. | |
| 6,013,062 A * | 1/2000 | Dilnik | 604/385.01 |
| 6,068,620 A | 5/2000 | Chmielewski | |
| 6,102,892 A | 8/2000 | Putzer et al. | |
| 6,120,485 A | 9/2000 | Gustafsson et al. | |
| 6,132,410 A * | 10/2000 | Van Gompel et al. | 604/385.25 |
| 6,156,951 A | 12/2000 | Gustafsson et al. | |
| 6,168,585 B1 * | 1/2001 | Cesco-Cancian | 604/385.26 |
| 6,183,458 B1 | 2/2001 | Ahlstrand et al. | |
| 6,217,563 B1 * | 4/2001 | Van Gompel et al. | 604/385.101 |
| 6,248,096 B1 * | 6/2001 | Dwork et al. | 604/349 |
| 6,258,077 B1 * | 7/2001 | Buell et al. | 604/393 |
| 6,264,641 B1 * | 7/2001 | Van Gompel et al. | 604/385.22 |
| 6,336,922 B1 | 1/2002 | Van Gompel et al. | |
| 6,361,527 B1 | 3/2002 | Van Gompel et al. | |
| 6,375,646 B1 | 4/2002 | Widlund et al. | |
| 6,547,774 B2 * | 4/2003 | Ono et al. | 604/385.29 |
| 2002/0007162 A1 * | 1/2002 | Cammarota et al. | 604/361 |
| 2002/0112982 A1 * | 8/2002 | Stagray et al. | 206/494 |
| 2002/0143311 A1 * | 10/2002 | Brisebois | 604/385.01 |
| 2002/0151864 A1 * | 10/2002 | Otsubo et al. | 604/385.29 |
| 2002/0169432 A1 * | 11/2002 | Fell et al. | 604/385.14 |

FOREIGN PATENT DOCUMENTS

| | | | |
|---|---|---|---|
| EP | 1 247 506 A | | 10/2002 |
| GB | 2218322 A | | 11/1989 |
| GB | 2253131 A | * | 9/1992 |
| GB | 2 268 389 A | | 1/1994 |
| JP | 03176053 | | 7/1991 |
| JP | 03205053 | | 9/1991 |
| WO | WO 99/49826 | | 10/1999 |
| WO | WO 02/091974 A | | 11/2002 |
| WO | WO 02091974 A1 | * | 11/2002 |

* cited by examiner

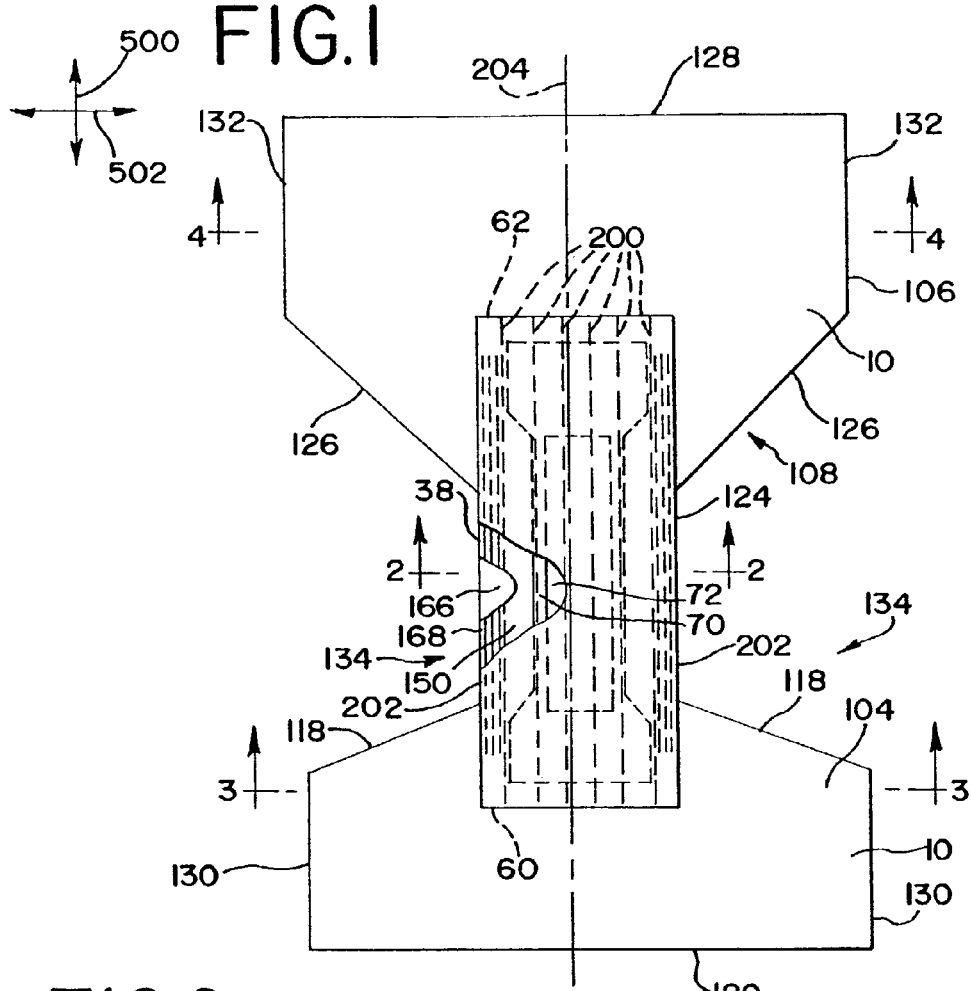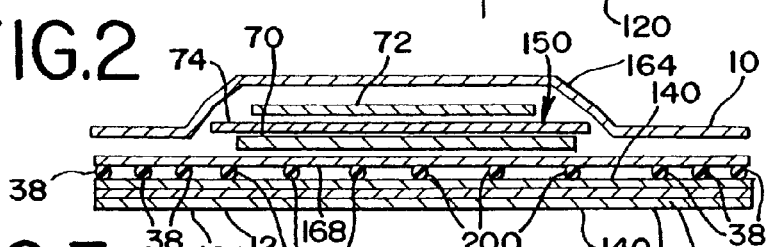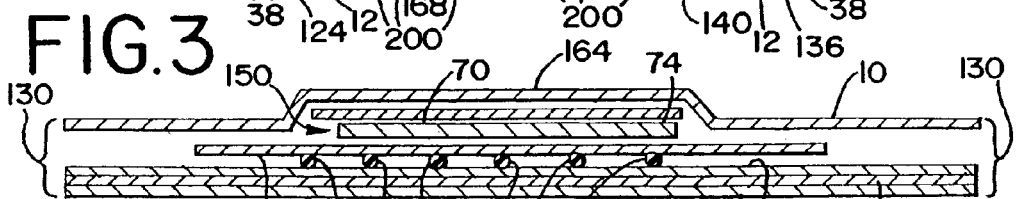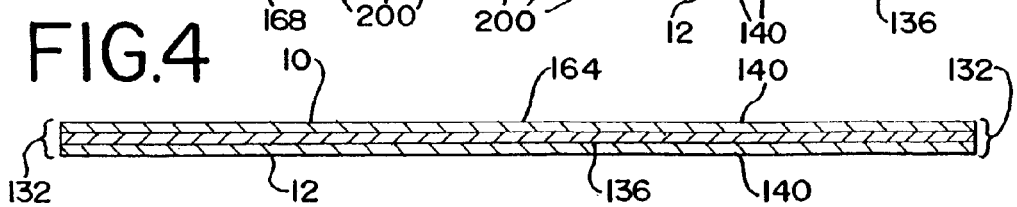

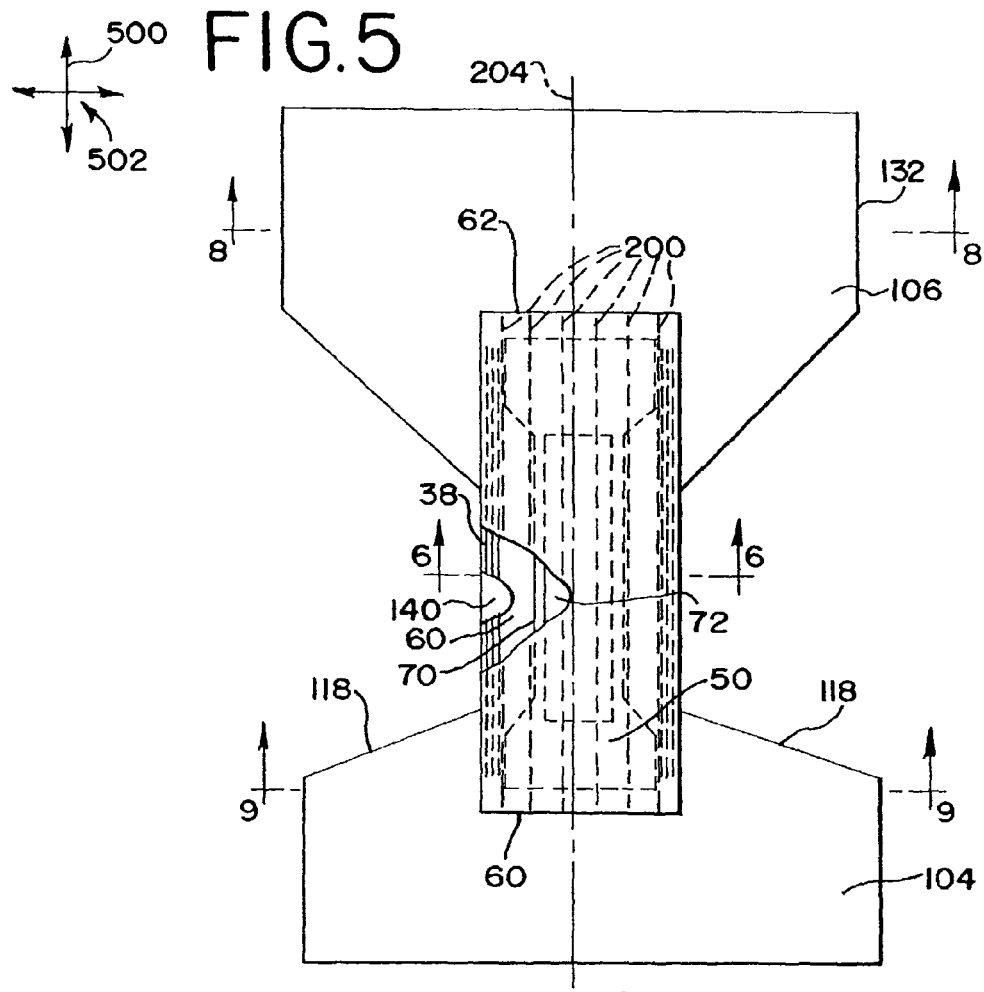
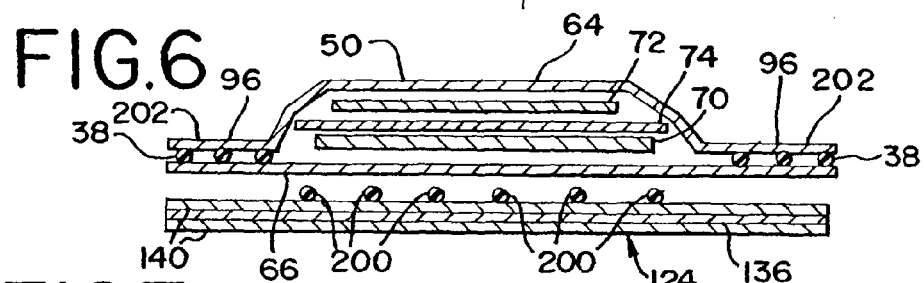
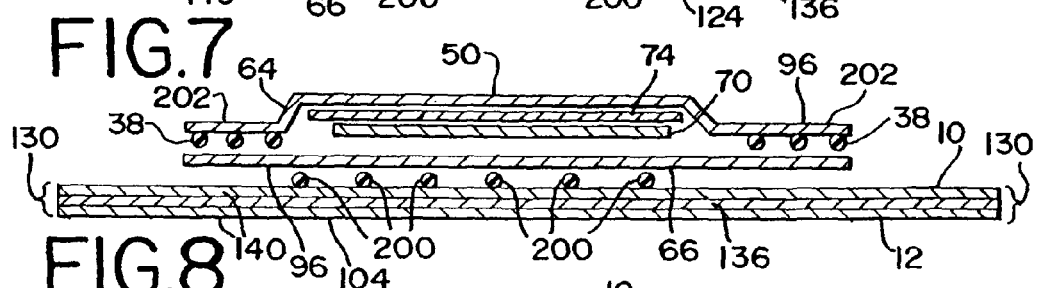
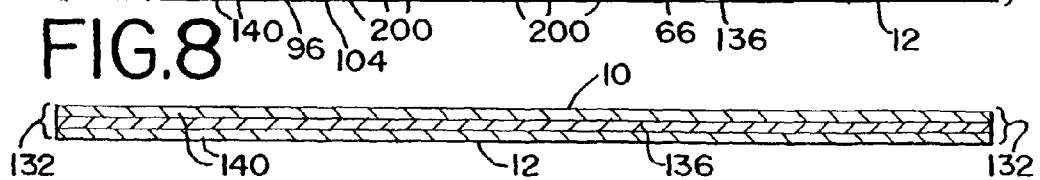

DISPOSABLE UNDERGARMENT WITH A DETACHABLE CROTCH MEMBER AND METHOD FOR THE USE THEREOF

BACKGROUND

The present invention relates generally to disposable undergarments, and in particular, to an undergarment having a detachable crotch member, and to the method for the use thereof.

Disposable undergarments can be configured in many different forms. For example, disposable absorbent garments can be configured as a pant-type, pull-on garment, or as a diaper-type product that is drawn up between the legs and fastened about the waist with various fastening systems. In some configurations, the garment is formed from a crotch member attached to a body panel, which may be elongatable. Often, the crotch member is secured across the entire width of the portion of the crotch member that overlaps the body panel. As such, the crotch member, which is often non-elongatable, can reduce or otherwise impede the elongation of the body panel, thereby reducing its ability to conform to the body of the user. In addition, the crotch member typically is not able to conform to the body of the user independently of the body panel, and can therefore distort the panels when fitted to a user.

Therefore the need remains for an improved undergarment that conforms to the body of the user during use without interference from a crotch portion thereof.

SUMMARY

Briefly stated, in one preferred embodiment described below, a disposable undergarment includes a body chassis member elongatable in at least a first direction between at least a first condition and second condition. The body chassis member has a greater elongation when in the second condition than when in the first condition. The disposable undergarment further includes a crotch member detachably connected to the body chassis member at at least one attachment location. At least a portion of the at least one attachment location is detached as the body chassis member is elongated between the first and second conditions. In one preferred embodiment, the crotch member includes an absorbent component.

In a preferred embodiment, the attachment location includes a plurality of attachment locations spaced apart in the first direction. In one preferred embodiment, the crotch member includes opposite side portions spaced apart in the first direction and a centerline disposed therebetween. Preferably, at least some of the plurality of attachment locations are spaced apart in the first direction between the centerline and one of the opposite side portions, with each of the plurality of attachment locations having a detachment strength. Preferably, the detachment strengths of the plurality of attachment locations spaced apart between the centerline and one of the opposite side portions become progressively stronger as one moves from the side portion toward the centerline.

In another aspect, a method of using a disposable undergarment includes providing an elongatable body chassis member in a relaxed condition and a crotch member detachably connected to said body chassis member at at least one attachment location. The method further includes elongating the body chassis member in a first direction from the relaxed condition to an elongated condition and thereby detaching the crotch member from the body chassis member at at least a portion of the at least one attachment location.

The various presently preferred embodiments provide significant advantages over other disposable undergarments, and methods for the use thereof. For example, the crotch member can be detached from the body chassis member as the body chassis member is elongated, for example as it is applied to the body of a user and conforms thereto. As the force for elongating the body panel exceeds the strength of attachment between the crotch member and the body chassis member, the crotch member detaches from the body chassis member so as to allow the undergarment, and the body chassis member in particular, to better conform to the body of the user. In this way, the body chassis member is provided with a greater range of elongation, thereby allowing it to suit a greater range of individual users. In the preferred embodiment, wherein the attachment locations define either a continuous or discontinuous attachment gradient, the crotch member progressively detaches from the body chassis member as the body chassis member is progressively elongated. In this way, the undergarment reacts to various users on an individualized basis to maximize the comfort and conformance thereof.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of layer thicknesses and the like, have been somewhat exaggerated for the sake of illustration and clarity.

FIG. 1 is a plan view of a first embodiment of a disposable undergarment taken from the bodyside thereof.

FIG. 2 is a schematic illustration of a cross-sectional view of the disposable undergarment taken along line 2-2 in FIG. 1.

FIG. 3 is a schematic illustration of a cross-sectional view of the disposable undergarment taken along line 3-3 in FIG. 1.

FIG. 4 is a schematic illustration of a cross-sectional view of the disposable undergarment taken along line 4-4 in FIG. 1.

FIG. 5 is a plan view of a second embodiment of a disposable undergarment taken from the bodyside thereof.

FIG. 6 is a schematic illustration of a cross-sectional view of the disposable undergarment taken along line 6-6 in FIG. 5.

FIG. 7 is a schematic illustration of a cross-sectional view of the disposable undergarment taken along line 7-7 in FIG. 5.

FIG. 8 is a schematic illustration of a cross-sectional view of the disposable undergarment taken along line 8-8 in FIG. 5.

DETAILED DESCRIPTION OF THE PRESENTLY PREFERRED EMBODIMENTS

Figure 9:
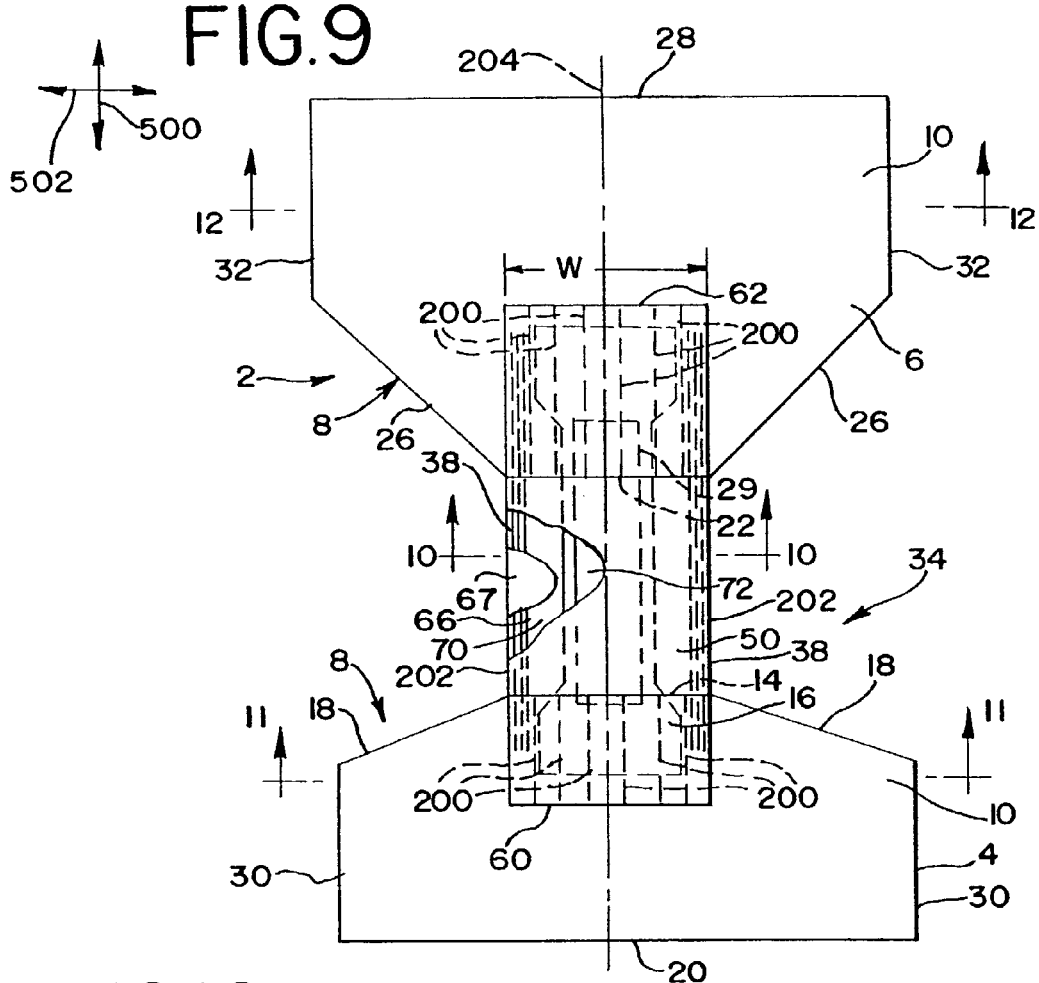
FIG. 9 is a plan view of a third embodiment of a disposable undergarment taken from the bodyside thereof.

It should be understood that the term "longitudinal," as used herein, means of or relating to length or the lengthwise direction 500. The term "laterally," as used herein, means situated on, directed toward or running from side to side. The term "first direction" generally refers to a path, line or course rather than a vector, and includes and applies equally to opposite orientations along the path, line or course, including for example and without limitation movement along a path, line or course in both directions (as indicated by the bi-directional arrows associated with the longitudinal and lateral directions 500, 502). Likewise, the term "second direction" generally refers to a path, line or course rather than a vector (not orientation dependent), and includes for example and without limitation movement along a path, line or course in both directions. In one example, the first direction is defined by and refers to one of the longitudinal and lateral directions, while the second direction refers to the other of the longitudinal and lateral directions.

The term "bodyside" should not be interpreted to mean in contact with the body of the user, but rather simply means the side that would face toward the body of the user, regardless of whether an undergarment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the undergarment is actually being worn by a user, regardless of whether any such outer garments are actually worn and regardless of whether there may be intervening layers between the component and any outer garment.

The term "machine direction" means the direction of flow as the various members and webs progress along the fabrication line and process. It should be understood that various separate members or webs can each be traveling in a machine direction, but with the various machine directions not necessarily being parallel or oriented in the same direction. For example, a first component such as a web may be traveling a first machine direction, which is substantially perpendicular to the travel of another component, such as an absorbent insert, in a second machine direction.

The term "cross direction" means the direction substantially perpendicular to the machine direction.

The term "downstream" means that one item is positioned more closely to the output or finished product end of the machine and/or process relative to another item. Conversely, the term "upstream" means that an item is positioned more closely to the input end of the machine or process relative to another item. For example, the output end is downstream of the input end, and vice versa, the input end is upstream of the output end.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The term "web" refers to a continuous stream of material, whether made from one or more layers or substrates, and regardless of whether it may have non-continuous, discrete items disposed thereon.

The terms "connecting," "coupled," "attached," and "secured," and variations thereof, broadly covers two or more items being directly connected one to the other, or by way of one or more intervening members or components.

Referring to FIGS. 9-12, an undergarment 2 has a body chassis member 8 that includes a first, front body panel 4 and a second, rear body panel 6. The terms "body chassis member" and "body panel" refer to the portion(s) of the undergarment, whether made of one or more layers or substrates or of one or more pieces or components, that is/are fitted circumferentially around the body of the user, for example about the waist region of the user, and/or one or more of the user's lower back, buttock, hips, crotch and abdomen.

The first and second body panels each have an inner, bodyside surface 10 and an outer, garment side surface 12. The first, front body panel 4 has a first edge 14 having a crotch portion 16 and leg opening portion 18 and a second terminal edge 20 that is linear in one embodiment but can assume other shapes. Likewise, the second, rear body panel 6 has a first edge 22 having a crotch portion 24 and a leg opening portion 26 and a second terminal edge 28, which is linear in one embodiment but can assume other shapes. Each of the first and second body panels have an outboard side edge 30, 32 formed along the outer periphery of the opposite side portions of the first and second body panel. It should be understood that the outboard side edges of the front and rear body panels could have different lengths relative to each other. Preferably, the edges 14, 22 of the first and second body panels are spaced apart in the crotch region so as to form a gap or space therebetween.

In alternative embodiments, shown in FIGS. 1 and 5, the body chassis member 108 extends substantially the entire length of the garment and defines and integrally forms the first, front body panel 104 and the second, rear body panel 106, as well as a crotch portion 124 extending therebetween. In this embodiment, with the front and rear body panels 104, 106 integrally formed with a crotch portion 124, the body panels have edges 118 that form portions of the leg opening, side edges 130, 132 and opposite terminal edges 120, 128.

In one embodiment, one or more, and preferably a plurality, meaning two or more, elastic elements are secured to each of the first and second body panels 4, 6, 104, 106. In one embodiment, a plurality of elastic elements are spaced across substantially the entire waist portion of the front and rear body panel, although they may be spaced across a lesser length. For example, elastic elements can extend along the upper waist portion and along the lower terminal edge defining in part a leg opening. Elastic elements 38 can also be secured along the sides of the crotch portion to provide a gasket with the user's legs.

In one embodiment, the front body panel has a "non-elasticized" area wherein there are no elastic elements, or other elastic or elastomeric backing members, incorporated therein or making up any portion of the thickness or cross-section of the body panel at that area. It should be understood, that in various preferred embodiments, one or more separate waist bands, with or without elastic elements, can be secured to one or both of the rear and front body panels, preferably along the upper terminal edges 20, 28, 120, 128 thereof. Likewise, one or more separate leg bands can be secured to one or both of the rear and front body panels along the edge 18, 26, 118, 126 of the body panel and/or along the edge of the crotch portion forming and defining the leg openings 34, 134. Alternatively, one or both of the body panels can be formed without any elastic elements.

The various waist and leg elastic elements can be formed from rubber or other elastomeric materials. One suitable material is a LYCRA® elastic material. For example, the various elastic elements can be formed of LYCRA® XA Spandex 540, 740 or 940 decitex T-127 or T-128 elastics available from E.I. duPont De Nemours and Company, having an office in Wilmington, Del.

Figure 12:
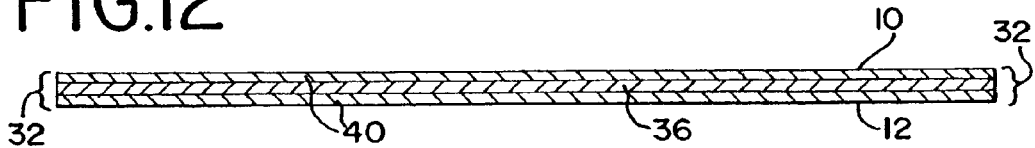
FIG. 12 is a schematic illustration of a cross-sectional view of the disposable undergarment taken along line 12-12 in FIG. 9.

Referring to FIGS. 4, 8 and 12, each body panel 4, 6, 104, 106 is formed as a composite, or laminate material, otherwise referred to as substrates or laminates, with one or more elastic elements 36, 136 sandwiched therebetween. The elastic element can be formed from various elastically stretchable materials, such as elastomeric films, bands, ribbons, threads and the like, which are disposed between opposite layers. In one embodiment, two or more layers 40, 140 are bonded to the elastic element 36, and/or each other, with various adhesives, such as hot melt, or by other techniques, including for example and without limitation ultrasonic bonding and heat pressure sealing. In one embodiment, the two layers are made of a non-woven material such as a spunbond material, a bonded carded material or other known materials. It should be understood that the body panels can be made of a single layer or substrate of non-woven material, or can be comprised of more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the body panel material can be secured to the elastic element(s), such as an elastically stretchable film, or elastomeric layer or elastic strands or ribbons, which have been elongated and retracted, such that the material is gathered when the elastic element(s) are relaxed. Alternatively, the material can be gathered and laminated to nonelongated elastic elements. In one preferred embodiment, the body panel includes a gathered elastic laminate made from nonwoven base sheets bonded with elongated elastic elements sandwiched therebetween.

In various preferred embodiments, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material that is elastomerically stretchable at least along one or both of the lateral article width and the longitudinal article length. Examples of such elastomeric composite materials can include a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary NBL, SBL, and NSBL materials are described in U.S. Pat. Nos. 5,226,992, 4,981,747, 4,965,122, 5,336,545, 5,385,775, 5,414,470, 4,720,415, 4,789,699, 4,781,966, 4,657,802, 4,652,487, 4,655,760, 5,116,662 and 5,114,781, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or MD/CD stretch characteristics, or that are extensible composites. Additional waist and leg elastic elements can be added to, but are not necessarily required by, the body panels.

As shown in FIGS. 1-12, in preferred embodiment, the entirety of the body panels 4, 6, 104, 106 are elasticized, such that the entire body panel elongates and conforms to the body of the user without any spacing between the body panel and the user's body, and without the attendant bulkiness of a non-elasticized material. As shown in the embodiment of FIG. 6, the crotch region 124 of the body chassis can also be elasticized.

Preferably, the body panels are breathable, cloth-like, multi-directional nonwoven laminates with stretch and/or extensible properties. In one preferred embodiment, the non-woven layers are pre-necked, preferably between about 10% and about 80%, in the longitudinal direction, which provides extensibility in the longitudinal direction with minimum force.

The terms "extensible," "extensibility," and variations thereof as used herein means capable of being extended, and providing a selected elongation, for example between about 5% and about 70%, when subjected to an applied tensile force. The body panel also is preferably capable of providing a selected, sustained deformation when subjected to an applied tensile force and then allowed to relax for a selected time period beginning immediately after removal of the tensile force. Preferably the sustained deformation is a substantially permanent deformation. The selected elongation and sustained deformation preferably occur at least along the longitudinal direction of the garment, although it should be understood that it also could occur along the lateral direction, or both. Various extensible materials, and other acceptable materials that can be used for the body panels are described for example in U.S. Pat. No. 6,217,563, issued Apr. 17, 2001 to Kimberly-Clark Worldwide, Inc., the same Assignee as the present application, the entire disclosure of which is hereby incorporated herein by reference.

The extensibility of the preferred non-woven material provides an increase in surface area without the retractive force of elastomeric materials. In one preferred embodiment, body panel is extensible in at least the cross-direction, or longitudinal direction, with the material providing an elongation of at least about 1 cm when subjected to a tensile force of 11.8 grams per cm. In addition, the body panel preferably provides a substantially permanent deformation of at least about 20% when it is subjected to a tensile force of 19.70 grams per cm and is then allowed to relax under a zero applied force for a period of 1 minute. Of course, it should be understood that the body panel can also be made extensible in the lateral direction.

In one embodiment, the body chassis member 8, 108 are made of non-woven laminates of two layers of longitudinally extensible 0.60 osy polypropylene spunbond material with elongated strands of Lycra® elastic sandwiched between the spunbond layers and thereafter adhesively bonded. In particular, the body panel material is necked in the cross direction. As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes. The elastics are then elongated in the machine direction and secured to the body panel material. The elastics are then allowed to retract so as to gather the necked spunbond material in the lateral (machine) direction thereby creating an elastically gathered non-woven body panel with longitudinal extensibility. The term "gather," and variations thereof, as used herein means puckered, or contracted into folds or wrinkles, which should be understood as including micropleats. In this way, the body panel can be elongated in both the longitudinal and lateral direction to conform to the body of the user when the garment is applied thereto. In particular, as the user pulls the garment up over their hips, the non-woven laminate body panels stretch in the lateral direction while the leg regions of the front and rear body panels conform to the crotch and body lines of the user. At the same time, the body panel material extends in the longitudinal direction to conform to the buttocks and stomach of the user. The extensibility of the body panels follows the natural curvature of the user's body to provide conformance thereto. As the body panel extends in the longitudinal direction, the spacing between the laterally extending elastic elements, incorporated in one preferred embodiment, will increase.

The body chassis non-woven material is preferably substantially hydrophobic, which may optionally be treated with a surfactant or otherwise processed to impart a desired level of wettability and hydrophilicity. In one particular embodiment of the invention, the body panel is a nonwoven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the Assignee of the present application.

Referring to FIGS. 1, 5 and 9, the crotch portion of the various undergarments connecting the front and rear body panels 4, 6, 104, 106, whether integrally formed or separately connected, can be folded such that the side edges 30, 32, 130, 132 of the front and rear body panels 4, 6, 104, 106 are aligned wherein they can be fixedly secured at a seam to form the leg opening 34, 134. The seam can be formed by bonding, sewing or otherwise attaching the side edges. Alternatively, the product can remain "open," wherein the body panels are releasably secured with one or more fastening members as explained below.

In one embodiment, the garment includes a combination of side edges that are secured to form a seam and fastening members that allow the fit of the undergarment to be adjusted. For example, in one embodiment, fastening members are preferably attached to the front body panel and extend inboard relative to the outboard side edge 30, 130 of the front body panel 4, 104 from an attachment location, which is preferably spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can comprise a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the undergarment can be broken along the lines of weakness after the garment is applied to a user, or beforehand. In one embodiment, the fastening members are secured to the garment-side surface of the body panel.

It should be understood that, in other embodiments, the fastening members can be secured to the rear body panel and engage the front body panel or, conversely, can be secured to the front body panel and engage the rear body panel, preferably along at least a portion that is not elasticized. In one embodiment, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

When incorporated into a disposable absorbent undergarment, the fastening members include a refastenable portion, such as an array of hook members, adhesives, such as pressure sensitive adhesives, buttons, zippers, snaps and other releasable and reattachable fastening devices. In various preferred embodiments, the fastening member includes one, two or more than two tab members. In one embodiment, the fastening members comprise a carrier member, which is preferably fixedly secured to the side portions of the front body panel with adhesive bonds, sonic bonds, thermal bonds, pinning, stitching or other known types of attachment. In alternative embodiments, the fastening members can be fixedly secured to the rear body panel or to one or both of the front and rear body panels, for example, at the seam, as explained above.

Referring to the various embodiments of FIGS. 1-12, the undergarment is disposable and is also configured as an absorbent undergarment. Referring to the embodiment of FIGS. 1-4, a crotch member 150 is disposed or sandwiched between a body side liner 164, which also forms part of the body chassis member 108, including the front and rear body panels 104, 106, and an outer cover 166, formed as a three-ply laminate. In this embodiment, the outer cover 166 includes inner and outer non-woven extensible substrates 140 with an elastic core 136 or element sandwiched therebetween. The body side liner 164 is liquid permeable and extensible. In one embodiment, the body side liner 164 is a necked stretchable material, but is not elastic.

Referring to the embodiments of FIGS. 5-12, the crotch member 50 is formed as a separate subassembly connected to a bodyside surface of the body chassis member 8, 108 (whether formed as a single integral member having a front and rear body panel and a crotch portion as shown in FIGS. 5-8, or as discrete and spaced apart front and rear body panel members as shown in FIGS. 9-12), rather than being sandwiched between layers thereof or integrated therein as shown in FIGS. 1-4. In any of the embodiments shown in FIGS. 1-12, the crotch member 50, 150 is preferably configured as an absorbent insert having first and second opposed terminal end edges 60, 62.

In the embodiments of FIGS. 5-12, the absorbent insert includes a substantially liquid permeable topsheet 64, or liner, and a substantially liquid impermeable backsheet 66, or outer cover. A retention portion 70 is disposed or sandwiched between the topsheet and the backsheet, which are connected. In the embodiment of FIGS. 1-4, the retention portion 70 is disposed or sandwiched between the bodyside liner 164 and the outer cover 166 of the body chassis member 108. In one embodiment, a barrier layer 168, or garment side liner, is secured to the retention portion 70 and is disposed between the retention portion and the outer cover 166.

Figure 10:
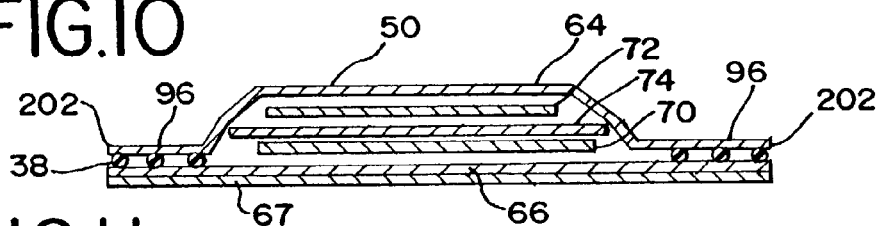
FIG. 10 is a schematic illustration of a cross-sectional view of the disposable undergarment taken along line 10-10 in FIG. 9.

In one embodiment, shown in FIG. 10, an outer cover member 67, such as a non-woven material, is secured to the backsheet 66 of the absorbent insert and forms part of the subassembly thereof. In one embodiment, the cover member 67 is formed as a breathable, stretched, thermal laminate material.

Referring to FIGS. 5-12, the topsheet 64, backsheet 66 and other components of the absorbent insert can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. Preferably, one or more crotch elastic members 38 are sandwiched between the top sheet 64 and backsheet 66.

Similarly, in the embodiment of FIGS. 1-4, crotch elastic members 38 are disposed between the outer cover 166 and the body side liner 164. It should be understood that the term "absorbent insert" refers to any material or assembly capable of absorbing liquids or bodily exudates, and may be comprised of a single material or component, for example a retention portion, or can be formed as a composite of several components. The absorbent insert can be made as a separate subassembly, or can be integrated into the body chassis member.

It should also be understood that the term "crotch member" refers to any member made of any material, including for example and without limitation those described herein with respect to the body panels and absorbent inserts, and is not limited to absorbent inserts and/or materials. For example, the crotch member may be made of one or more layers of a non-woven material, but also includes for example and without limitation the retention portion, alone and in combination with the barrier liner 168, backsheet 66, 166 and top sheet 64, 164, and/or any other components.

In one preferred embodiment, as shown in FIGS. 1-12, additional layers, including for example, a liquid acquisition/distribution layer 72, otherwise referred to as a surge or transfer layer, are also preferably incorporated into the absorbent insert. Preferably, the surge layer does not run the entire length of the absorbent insert and is shorter than the retention portion. The topsheet can be indirectly joined to the backsheet by affixing the topsheet to intermediate layers, such as the surge layer or retention portion, which in turn is affixed to the backsheet. The absorbent insert also may include barrier cuffs, or leakage control shields, formed along the opposite longitudinally extending edges of the absorbent composite.

The backsheet is preferably liquid impermeable, but may be liquid permeable, e.g., when an additional barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the topsheet 64 of FIGS. 5-12 and the bodyside liner 164 of FIGS. 1-4 can comprise various woven or nonwoven materials. For example, the topsheet and liner can be composed of a meltblown or spunbonded web of desired fibers, and may also be a bonded-carded web. The topsheet and liner can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like. In one embodiment, the liner 164 is an extensible/stretchable, necked nonwoven material.

In various constructions, the backsheet 66 of FIGS. 5-12 or the barrier liner 168 of FIGS. 1-4 can be formed of various materials, including various films, and can include a woven or nonwoven fibrous web layer, for example a breathable, stretched, thermal laminate, which can be treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers) . A material of this type has been employed to form the outercover of a HUGGIES® Ultratrim Disposable Diaper, which has been commercially available from Kimberly-Clark Corporation. As explained above, the backsheet can provide the outercover of the article, particularly in the crotch region. Optionally, however, the article may include a separate outercover component member, as disclosed herein, which is additional to the backsheet. The outercover can be joined, for example, to one or more of the absorbent composite and/or body panels as explained above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet and/or outercover also can be extensible. In one preferred embodiment, the backsheet and/or outercover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet and/or outercover also can be expandable, for example when it has one or more folds, e.g., one or more z-folds (not shown), or can be both extensible and expandable. The term "expandable" as used herein means to enlarge or to increase the extent or area, lateral and/or longitudinal, thereof, e.g., by unfolding one or more folds. The term "elongate," and variations thereof, as used herein means to lengthen or enlarge, whether by extension, expansion, or stretching, or any combination thereof.

The retention portion 70 is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, Weyerhauser NB416 or ND416, available from Weyerhauser, Inc., of Seattle, Wash., or Drytech® 2035M materials available from Dow Chemical Co. of Midland, Mich., or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. Nos. 5,147,343 for Absorbent Products Containing Hydrogels With Ability To Swell Against Pressure, 5,601,542 for Absorbent Composite, and 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion preferably can be made of a single or dual layer of absorbent material. The retention portion preferably has an hour-glass shape with enlarged end regions. Alternatively, the retention portion can include a folded or multi-layered configuration. The retention portion preferably has a length substantially equal to, or slightly shorter than, the length of the absorbent insert. The retention portion can include one or more barrier layers attached to the absorbent material. In one embodiment, an upper tissue substrate 74 is disposed adjacent the retention portion. Alternatively, a lower tissue substrate can be disposed adjacent an opposite side of the retention portion, or the tissue can completely envelope the retention position.

Figure 11:
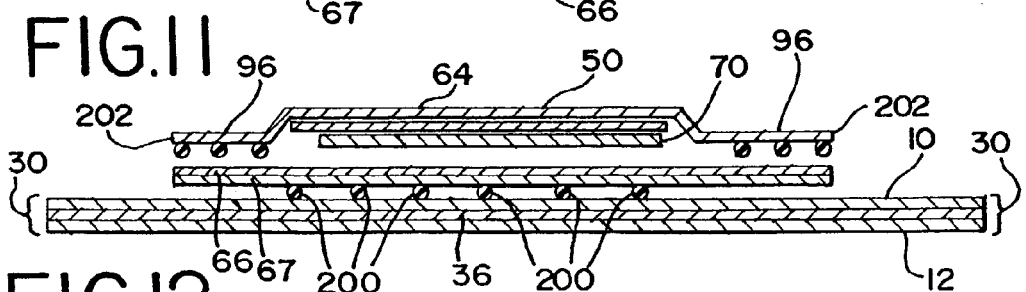
FIG. 11 is a schematic illustration of a cross-sectional view of the disposable undergarment taken along line 11-11 in FIG. 9.

Referring to FIGS. 9-12, and in particular FIGS. 9 and 11, the opposite garment side of the end regions of the crotch member 50, and in particular, the outer, garment side surface of the backsheet 66, are connected to the bodyside surface of the opposed crotch portions 16, 24 of the first and second body panels 4, 6. It should be understood that in an alternative preferred embodiment, the crotch member, for example the body side thereof, can be connected to the garment side surface of the first and second body panels. It should be understood that the crotch member 50 can be secured using any of the methods of attachment described above, including for example various adhesives, stitching or other bonding methods. The crotch member can be secured to the body panels with any configuration of attachment lines, swirls, patterns, spots, etc., or can be a full and continuous attachment therebetween.

In one embodiment (not shown), the entire portion of the crotch member overlapping the body panels is attached thereto with a continuous attachment across the width (W) of the crotch member. Preferably, at least a portion of the continuous attachment is detachable, for example from the opposite side edges of the crotch member towards a centerline thereof. In this way, the crotch member can be progressively detached from the body chassis member from the outer side portions moving inward as a greater shear force is applied to the attachment location by virtue of a tensile force being applied to the body chassis member as the undergarment is applied to the user. In one preferred embodiment, the strength of the continuous attachment between the crotch member and the body chassis gets progressively stronger as it moves from the opposite sides of the crotch member toward the centerline thereof.

In one embodiment, shown in FIGS. 6, 7 and 11, the crotch member 50, and in particular the garment side surface of the backsheet 66, is detachably connected to the body side surface of the body chassis member 8, 108, 4, 104, 124 at a plurality of, meaning two or more, discrete attachment locations 200 that are laterally spaced apart between opposite side portions 202 of the crotch member 50.

In the embodiment of FIGS. 1-4, the garment side of the barrier layer, or liner 168, which is secured to the retention portion 70, is detachably connected to the bodyside surface of the outer cover 166. In one embodiment, the body side liner 164 is attached to the crotch member 150, including the acquisition/distribution layer 72 and the retention portion 70. In other embodiments, the liner 164 is not attached to the various crotch member components.

In one exemplary embodiment, shown in FIGS. 2, 3, 6, 7, and 11, six attachment locations 200 are spaced apart in the lateral direction between the side portions 202 of the crotch member 50, 150. As shown in FIGS. 1, 5 and 9, the six attachment locations 200 includes pairs of attachment locations equally spaced on opposite sides of the centerline 204. Of course, more or less attachment locations would also work. The attachment locations 200 are symmetric relative to the centerline 204 in the illustrated embodiments, although it should be understood that they may be non-symmetric relative thereto.

In one embodiment, the attachment between the crotch member 50, 150 and the body chassis member 8, 108 at each attachment location 200 gets progressively stronger as the locations move inwardly from the opposite side portions 202 of the crotch member to a centerline 204 of the crotch member. For example, the width or the surface area of each attachment location 200, wherein the attachment is preferably made by one or more of an ultrasonic, thermal or adhesive bond, can be progressively increased as the locations move inwardly from the opposite side portions 202 of the crotch member to the centerline 204. In one embodiment, it should be understood that the attachment between the crotch member 50,150 and the body chassis member 8, 108 at one or more of the attachment locations 200, for example and without limitation, proximate the centerline 204, may not be detachable, meaning that the attachment between the crotch member and the body chassis is stronger than the force required to tear one or both of the body chassis material and crotch member. Alternatively, it should be understood that all of the attachments can be made detachable, and also that they can be of equal strength. In various embodiments, the attachment strength can vary from a minimal attachment achieved for example by mechanical attachment (e.g., hook and loop fasteners), adhesive add-on (spray), or heat or ultrasonic point bonding, to a maximum attachment achieved by hot melt adhesive coating, solid thermal bonding or ultrasonic bonding.

It should be understood that the various attachment configurations shown in FIGS. 7 and 11, which illustrate the crotch member 50 and front body panel 4, 104, apply equally to the attachment configuration between the rear body panel 6, 106 and the crotch member. It should be understood, however, that the crotch member 50 may be detachably connected to one or the other of the body panels 4, 6, 104, 106 (or crotch portion 124) of the body chassis member 8, 108, and may be non-detachably connected to other portions of the body chassis member. Alternatively, the crotch member may not be connected at all to one or the other of the body panels (or crotch portion) of the body chassis member.

Referring to the embodiments of FIGS. 5-12, the outermost attachment location 200 preferably is spaced inboard of the outer edge 202 of the crotch member 50 so as to form an unattached side margin 96, which functions as a flap while maximizing the ability of the underlying body panel to elongate and conform to the body of the user. Preferably, the attachment locations 200 run the entirety of the length of the portion of the crotch member 50 overlapping the corresponding body chassis member, although it should be understood that the attachment locations could be less than such a length, or comprise intermittent portions of attachment along each attachment location or line. Accordingly, in the embodiment of FIGS. 9-12, the attachment locations 200 extend longitudinally along the end portions of the crotch member, while in the preferred embodiments of FIGS. 1-8, the attachment locations 200 extend the entire length of the crotch member.

In operation, the user applies the undergarment to their body, whether by way of pulling it up around their waist as a pant-like garment or by way of fastening it about their waist with fasteners as a diaper-like garment. As the garment is applied or fitted to the body of the user, the body chassis member 8, 108, and especially the front and rear body panels, are elongated from a first condition, preferably relaxed, to a second condition, preferably elongated, in at least one direction, preferably the lateral direction 502. Of course, the body chassis member 8, 108 can also elongate in the longitudinal direction 500 from the crotch to the waist. Preferably, the body chassis member 8, 108, and in particular one or the other of the body panels 4, 6, 104, 106, is elongated between about 20% and about 300%, alternatively between about 50% and about 250%, and alternatively between about 75% and about 200%, as it is applied to the user. The body chassis member 8, 108 is elongated by virtue of a tensile force being applied thereto as the body chassis member conforms to the body of the user.

Figure 13:
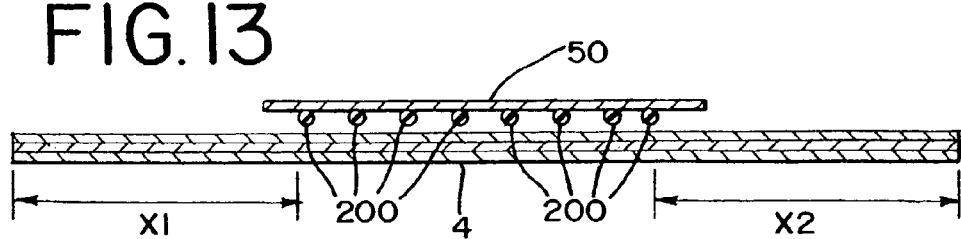
FIG. 13 is a schematic illustration of one attachment configuration between a crotch member and a body chassis member.
Figure 14:
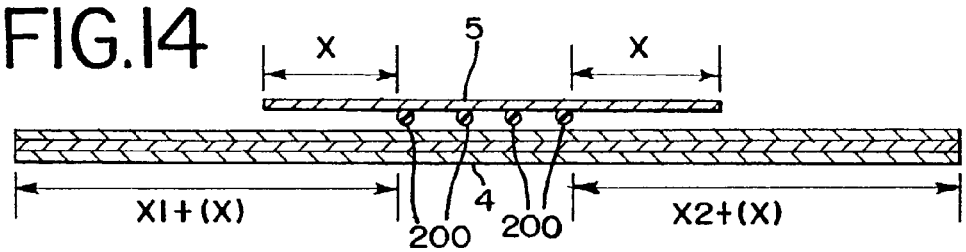
FIG. 14 is a schematic illustration of another attachment configuration between a crotch member and a body chassis member.
Figure 15:
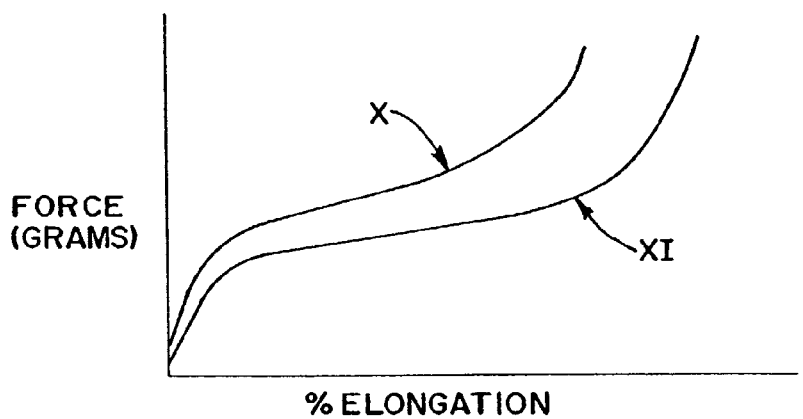
FIG. 15 is a stress/strain curve for the body chassis members shown in FIGS. 13 and 14.

The detachable bonds at locations 200 secure the substantially non-elastic crotch member 50, 150 and the elastic body chassis, more specifically the body panels 4, 6, 104, 106. The detachable bonds increase the elongation of the garment, or fit range thereof, by allowing for the user of a greater amount of the surface area of the elastic body panels. Accordingly, in one embodiment, the detachment strength of the relative detachable bond is less than the highest force (force/cm per width) required to elongate the elastic body panel, such that the bonds can detach, but greater than the lowest force required to elongate the body panel, such that the bonds maintain their attachment during at least a portion of the use of the garment. Referring to FIGS. 13 and 14, two embodiments of a crotch member 50 attached to a body panel 4 are shown. In the first embodiment of FIG. 13, a greater cross-sectional width or area of the crotch member is attached, by virtue of attachments 200, than in the second embodiment shown in FIG. 14. Accordingly, the stress/strain curve for the unattached body panel width X=X1+X2 of the embodiment in FIG. 13 requires a greater force to achieve a certain predetermined elongation than does the unattached body panel width XI=X1+X2+2x. In one aspect, the embodiment of FIG. 14 corresponds to the embodiment of FIG. 13 with the outer attachment locations being detached. In the FIG. 14 embodiment, a greater percent elongation is achieved for a single predetermined force applied to the body panel 4.

As the body chassis member 8, 108 is elongated, with the attendant application of a tensile force, the body chassis member applies a shear force to the attachment 200 between the crotch member 50, 150, which is preferably not substantially elongatable or has substantially different elongation properties as compared with the body chassis member and in particular the body panels. For example, the crotch member may require substantially greater tensile forces to achieve an equivalent amount of percent elongation as the body chassis material.

In the preferred embodiments, the shear forces applied between the crotch member 50, 150 and the body chassis member 8, 108, due to the elongation differential, detach the crotch member from the body chassis member at the attachment locations 200. The shear forces are first applied at the outboard attachment locations adjacent the side portions 202 of the crotch member. The shear force required to detach the crotch member from the body chassis member at the various attachment locations is preferably less than a predetermined tensile force required to elongate the body chassis member a desired amount. It should be understood that the tensile force is preferably applied equally on both sides of the crotch member. Accordingly, the attachment locations 200 are preferably arranged symmetrically relative to the centerline 204 of the crotch member and function in pairs on opposite sides thereof. Therefore, the outermost attachments 200 preferably are configured to shear or detach in response to a similar shear force, with subsequent next inner pairs functioning together and so on. Of course, it should be understood that the attachment locations can be nonsymmetrical, in location or shear strength.

As explained above, the attachments 200 are preferably made stronger and more resistant to shear as the locations move inboard from the outer side portions 202 of the crotch member toward the centerline 204 thereof. In this way, successively higher tensile forces are required to shear the attachments at successive attachment locations and thereby successively detach the crotch member from the body chassis member. In addition, the tensile force applied to the body chassis member successively rises and falls (in an amount less than the preceding rise), with the tensile force initially spiking until the outmost attachment locations shear so as to thereby relax the body chassis member slightly as the portion thereof between the sheared attachment and the next attachment location is allowed to elongate. The tensile force then spikes again until the next inner attachments are sheared, again with a resultant relaxing of the body chassis member as the portion thereof between the sheared attachments and the next attachment locations are allowed to elongate. This pattern is followed until each attachment between the crotch member and the body chassis member is at least partially detached at all of the attachment locations 200, or until the detaching shear force is greater than the strength of the body chassis member or the crotch member such that one of those members experiences failure.

Since, in the preferred embodiment, the strengths of the attachments between the crotch member 50, 150 and the body chassis member 8, 108 at the attachment locations 200 preferably increase as the attachment locations move inboard toward the centerline 204, the tensile forces required to break the next inboard attachments also successively increase. In this way, the undergarment is preferably configured with a discontinuous attachment gradient between the crotch member 50, 150 and body chassis member 8, 108. As such, the undergarment will automatically and independently adjust and conform to the body of any particular user. For example, for larger users, the elongation of the body chassis member in certain regions will be relatively large, for example in the longitudinal direction, so as to thereby generate relatively large tensile forces. Those tensile forces in turn will successively shear the attachment between the crotch member and the body chassis member at various attachment locations, thereby allowing the body chassis to elongate a greater amount. In contrast, for smaller users, the elongation of the body chassis member will not be as great, and the resultant tensile forces will not be sufficient to detach the crotch member from the body chassis member at all of the attachment locations.

Of course, it should be understood that all of the attachment locations can be configured with the same attachment strength. It also should be understood that in such an embodiment, the subsequent relaxation of the body chassis member after each detachment will still provide for a successive rather than a simultaneous failure of the various attachment locations depending on the size of the user and the attendant elongation of the body chassis member.

It should be understood that during use, only a portion of the attachment between the crotch member and the body chassis member at each attachment location may detach. For example, the opposite ends of the crotch member may detach from the body chassis member at several or all of the attachment locations, wherein the tensile forces (and corresponding shear forces) being applied are the greatest due to a greater elongation of the body chassis. At the same time, other portions of the crotch member (for example the middle portion thereof at the crotch region) may remain attached to the body chassis member at those same attachment locations during the entire use cycle of the garment, since the tensile forces (and corresponding shear forces) are minimal or non-existent in those regions due to the lack of elongation in the lateral direction.

Figure 16:
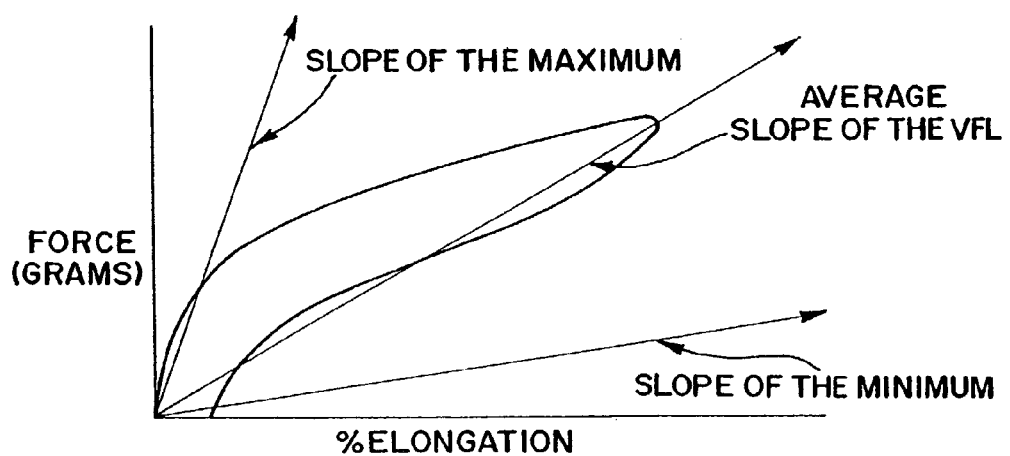
FIG. 16 is a stress/strain curve for an exemplary body chassis material.
Figure 17:
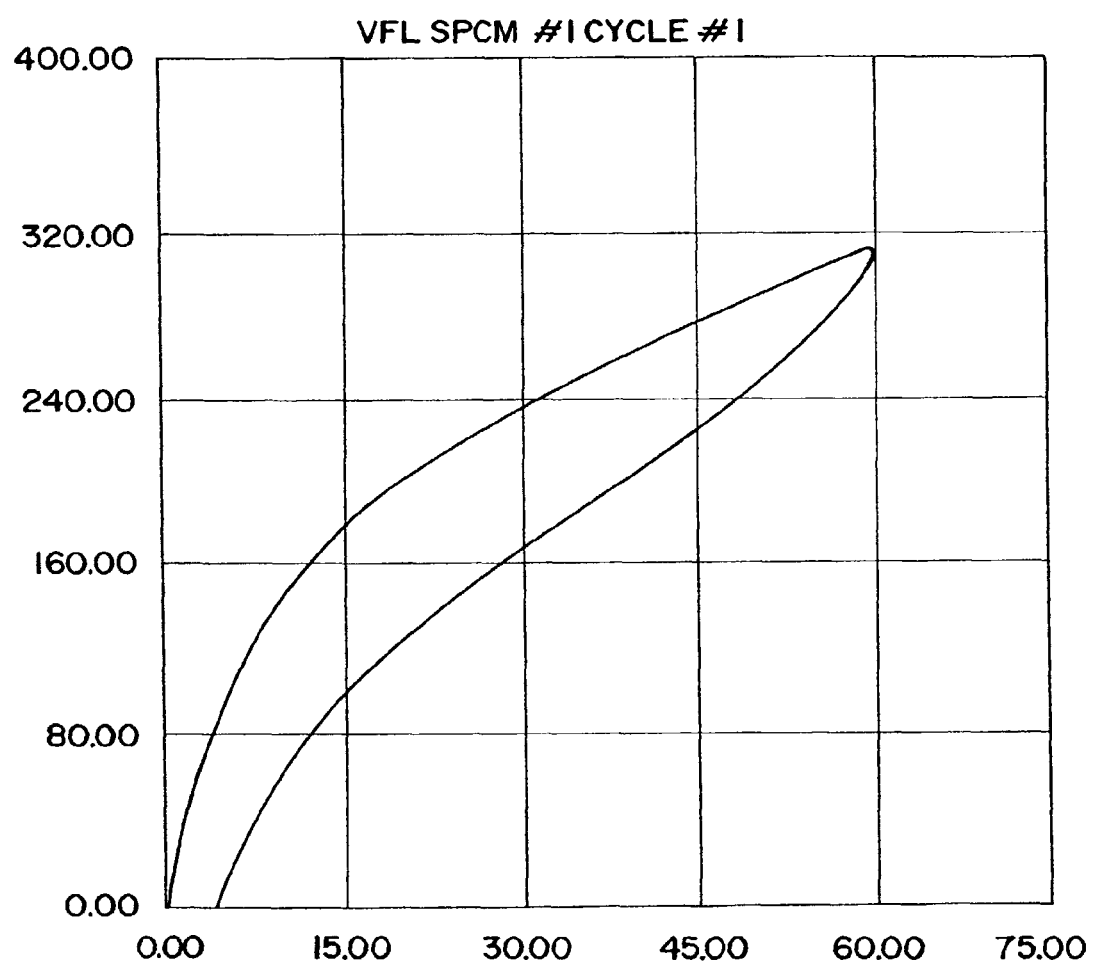
FIG. 17 is a stress/strain curve for the body chassis material shown in FIG. 16.

Referring to FIGS. 16 and 17, a stress/strain curve is shown for a body panel made of a vertical filament laminate (VFL) having Kraton® strands positioned between about 3 and 4 mm apart, elongated to 200%, and adhesively laminated to top and bottom non-woven layers. The laminate structure is allowed to retract prior to winding the material onto a roll. Because the Kraton® strands are a thermoplastic material, which are adhesively laminated to two non-woven layers, the stress/strain curve is not linear on the extension or retraction sections of the curve. Accordingly, the force to detach the bonds corresponds to the differences in the force to elongate the VFL elastic laminate.

The stress/strain curves were developed from a test of the VFL material as follows:

Test Procedure (One-Cycle Tensile Test (without hold time)):

1. A 2 inch wide by 5 inch long specimen was cut from a sheet of sample VFL material. The stretchable direction of the material was in the length direction of the specimen, which is also the test direction.
2. The one-cycle tensile test was conducted on a tensile tester (Model: Synergie 200 available from MTS) located in a room where the temperature was maintained at 23 degrees C. and with a relative humidity at 50%.
3. The distance between the lower and upper jaws of the tensile tester were set at 3 inches.
4. The jaws were clamped onto the specimen.
5. The moving (upper) jaw was activated to travel at a constant rate of 5 inches/minute away from the stationary (lower) jaw. The moving jaw was stopped at an extension of 1.8 inches (60% extension).
6. The moving jaw then returned immediately to its initial starting position at a rate of 5 inches/minute.
7. The load v. % strain for the tension and retraction cycle was recorded on a computer equipped with TestWorks Version 3.10 software program available from MTS.

As set forth in the attached Table 1, an average slope of the VFL material was calculated as being 300 grams/4.57 cm, which is 66 grams/cm for a 2.00 inch (5 cm) wide sample. Accordingly, as illustrated in FIG. 16, the maximum slope for the exemplary VFL material can be as high as 300 grams/cm or the minimum slope can be as low as 10 grams/cm for a 2 inch wide sample.

TABLE 1

VFL Material Force to Elongate

| Elongation | Distance (cm) | Force (grams) | Ratio: Force/distance (grams/cm) |
|---|---|---|---|
| 15% | 1.14 | 170 | 149 |
| 30% | 2.28 | 240 | 105 |
| 45% | 3.43 | 280 | 81 |
| 60% | 4.57 | 300 | 66 |

Accordingly, the detachment strength (Ds), or the force required to detach the body panel from the crotch member at any particular attachment location, should fall into one of the following ranges (assume results for a 2 inch wide sample) (1)

20 grams/cm<Ds<300 grams/cm; (2) 40 grams/cm<Ds<200 grams/cm; (3) 60 grams/cm<Ds<100 grams/cm. Of course, it should be understood that the detachment strength (Ds) is dependent on the area of attachment (Aa (area)) and the attachment strength (As (force/area).

$$Ds=(Aa)(As).$$

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A disposable undergarment comprising:
a body chassis member elongatable in at least a first direction between at least a first condition and second condition, wherein said body chassis member has a greater elongation when in said second condition than when in said first condition; and
a crotch member detachably connected to said body chassis member at a plurality of detachable attachment locations, wherein at least a portion of each of said plurality of attachment locations is detachable from an attached configuration to a detached configuration in response to said elongation of said body chassis member between said first and second conditions;
wherein said crotch member comprises opposite side portions spaced apart in said first direction and a centerline disposed therebetween, wherein at least two of said plurality of detachable attachment locations are spaced apart in said first direction between said centerline and one of said opposite side portions, and wherein each of said at least some of said plurality of detachable attachment locations have a detachment strength, wherein said detachment strengths of said at least some of said plurality of detachable attachment locations spaced apart between said centerline and said one of said opposite side portions become progressively stronger between said one of said opposite side portions and said centerline.

2. A disposable undergarment comprising:
a body chassis member elongatable in at least a first direction between a relaxed condition and an elongated condition in response to an application of a tensile force in said first direction; and
a crotch member connected to said body chassis member at a plurality of attachment locations spaced apart in said first direction, wherein said crotch member is detachable from said body chassis member at at least a portion of one of said plurality of attachment locations in response to an application of a detaching shear force in said first direction, wherein said tensile force is greater than said detaching shear force, wherein said crotch member comprises opposite side portions spaced apart in said first direction and a centerline disposed therebetween, wherein at least two of said plurality of attachment locations are spaced apart in said first direction between said centerline and one of said opposite side portions, and wherein each of said at least some of said plurality of attachment locations have a detachment strength, wherein said detachment strengths of said at least some of said plurality of attachment locations spaced apart between said centerline and said one of said opposite side portions become progressively stronger between said one of said opposite side portions and said centerline.

3. A method of using a disposable undergarment comprising:
providing an elongatable body chassis member in a relaxed condition and a crotch member detachably connected to said body chassis member at a plurality of detachable attachment locations spaced apart in a first direction;
elongating said body chassis member in said first direction from said relaxed condition to an elongated condition;
and thereby detaching said crotch member from said body chassis member at at least a portion of at least one of said plurality of detachable attachment locations in response to said elongating said body chassis member in said first direction;
wherein said crotch member comprises opposite side portions spaced apart in said first direction and a centerline disposed therebetween, wherein at least some of said plurality of detachable attachment locations are spaced apart in said first direction between said centerline and one of said opposite side portions and wherein said plurality of detachable attachment locations each have a detachment strength, wherein said detachment strengths of said at least some of said plurality of detachable attachment locations spaced apart between said centerline and said one of said opposite side portions become progressively stronger between said one of said opposite side portions and said centerline, and wherein said detaching said crotch member from said body chassis member at said at least said portion of said at least one of said plurality of attachment locations comprises successively detaching said crotch member from said body chassis member at at least some of said plurality of detachable attachment locations between said one of said opposite side portions and said centerline.

4. The method of claim 3 wherein said body chassis member comprises an outer cover defining front and rear body panels and a crotch portion extending therebetween, and wherein said crotch member comprises an absorbent insert.

5. The method of claim 4 wherein said body chassis further comprises an body side liner connected to said outer cover with said absorbent insert sandwiched therebetween.

6. The method of claim 4 wherein said absorbent insert is secured to a bodyside surface of said outer cover.

7. The method of claim 3 wherein said body chassis member comprises a front body panel and a rear body panel each having a terminal crotch edge, wherein said terminal crotch edges of said front and rear body panel are spaced apart in a second direction so as to form a gap therebetween, and wherein said crotch member bridges said gap and includes opposite end portions overlying and secured to said front and rear body panels, wherein at least one of said opposite end portions of said crotch member is detachably connected to at least one of said front and rear body panels at said at least one attachment location.

8. The method of claim 7 wherein each of said opposite end portions of said crotch member are detachably connected to said front and rear body panels at at least one front attachment location and at at least one rear attachment location respectively.

9. The method of claim 3 wherein elongating said body chassis member in said first direction from said relaxed condition to said elongated condition comprising applying a tensile force to said body chassis member in said first direction, and wherein said detaching said crotch member from said body chassis member at said at least said portion of said at least one attachment location comprises applying a shear force between said crotch member and said body chassis member at said at least said portion of said at least one attachment location, wherein said tensile force is greater than said shear force.

10. The disposable undergarment of claim 1 wherein said at least one attachment has a detachment strength of between 20 grams/cm and 300 grams/cm.

11. The disposable undergarment of claim 2 wherein said at least one attachment location has a detachment strength of between 20 grams/cm and 300 grams/cum.

12. The disposable undergarment of claim 1 wherein said crotch member is detachably connected to said body chassis member at said at least one attachment location when said body chassis member is in said first condition, wherein said first condition is a relaxed, unstretched condition.

13. The disposable undergarment of claim 2 wherein said crotch member is detachably connected to said body chassis member at said at least one attachment location when said body chassis member is in said first condition, wherein said first condition is a relaxed unstretched condition.

14. The disposable undergarment of claim 1 wherein said crotch member comprises at least a retention portion and a layer separate from said retention portion, wherein said layer is detachably connected to said body chassis member, and wherein said retention portion and said layer both comprise free edges spaced apart in said first direction and defining the outermost side portions of said retention portion and said layer respectively, with said retention portion and said layer are both free of any longitudinally extending folds allowing expansion of said retention portion and said layer in said first direction.

15. The disposable undergarment of claim 2 wherein said crotch member comprises at least a retention portion and a layer separate from said retention portion, wherein said layer is detachably connected to said body chassis member, and wherein said retention portion and said layer both comprise free edges spaced apart in the first direction and defining the outermost side portions of said retention portion and said layer respectively, with said retention portion and said layer are both free of any longitudinally extending folds allowing expansion of said retention portion and said layer in said first direction.

16. A disposable undergarment comprising:
a body chassis member elongatable in at least a first direction between at least a first condition and second condition, wherein said body chassis member has a greater elongation when in said second condition than when in said first condition; and
a crotch member detachably connected to said body chassis member at at least one attachment location, wherein at least a portion of said at least one attachment location is detachable from an attached configuration to a detached configuration in response to said elongation of said body chassis member between said first and second conditions, and wherein said at least one attachment location extends longitudinally along a second direction substantially perpendicular to said first direction, wherein a portion of said crotch member overlaps said body chassis member, wherein said at least one attachment location extends longitudinally along said second direction an entire length of the overlapping portion of the crotch member and said body chassis member.

17. The disposable undergarment of claim 1 wherein said at least one attachment location is formed in a linear configuration having an overall length greater than a width thereof.

18. The disposable undergarment of claim 1 wherein said at least one attachment location comprises a plurality of intermittent portions of attachment longitudinally spaced apart along said second direction.

19. A method of using a disposable undergarment comprising:
providing an elongatable body chassis member in a relaxed condition and a crotch member detachably connected to said body chassis member at at least one attachment location, wherein a portion of said crotch member overlaps said body chassis member, wherein said at least one attachment location extends longitudinally along said second direction an entire length of the overlapping portion of said crotch member and said body chassis member; and
elongating said body chassis member in a first direction from said relaxed condition to an elongated condition; and
thereby detaching said crotch member from said body chassis member at at least a portion of said at least one attachment location in response to said elongating said body chassis member in said first direction, wherein said at least one of said plurality of attachment locations location extends longitudinally along a second direction substantially perpendicular to said first direction.

20. The method of claim 3 wherein said at least one attachment location is formed in a linear configuration having an overall length greater than a width thereof.

21. The method of claim 3 wherein said at least one attachment location comprises a plurality of intermittent portions of attachment longitudinally spaced apart along said second direction.

22. The method of claim 3, wherein said detachment strengths are each between 20 grams and 300 grams per five centimeters of width in accordance with Test Procedure.

23. The article of claim 1, wherein said detachment strengths are each between 20 grams and 300 grams per five centimeters of width in accordance with Test Procedure.

24. The article of claim 2, wherein said detachment strengths are each between 20 grams and 300 grams per five centimeters of width in accordance with Test Procedure.

25. The disposable undergarment of claim 1 wherein said at least one attachment location extends longitudinally along a second direction substantially perpendicular to said first direction.

26. The disposable undergarment of claim 1 wherein said first condition is a relaxed condition.

27. The disposable undergarment of claim 1 wherein said crotch member remains attached to said body chassis member at at least one of said plurality of attachment locations as said body chassis member is elongated between said first and second conditions.

28. The disposable undergarment of claim 1 wherein said body chassis member comprises an outer cover defining front and rear body panels and a crotch portion extending therebetween, and wherein said crotch member comprises an absorbent insert.

29. The disposable undergarment of claim 28 wherein said body chassis further comprises a body side liner connected to said outer cover with said absorbent insert sandwiched therebetween.

30. The disposable undergarment of claim 28 wherein said absorbent insert is secured to a bodyside surface of said outer cover.

31. The disposable undergarment of claim 1 wherein said body chassis member comprises a front body panel and a rear body panel each having a terminal crotch edge, wherein said terminal crotch edges of said front and rear body panel are spaced apart in a second direction so as to form a gap therebetween, and wherein said crotch member bridges said gap and includes opposite end portions overlying and secured to said front and rear body panels, wherein at least one of said opposite end portions of said crotch member is detachably connected to at least one of said front and rear body panels at said at least one attachment location.

32. The disposable undergarment of claim 31 wherein each of said opposite end portions of said crotch member are detachably connected to said front and rear body panels at at least one front attachment location and at at least one rear attachment location respectively.

33. The disposable undergarment of claim 1 wherein said body chassis member is elongatable between said at least said first condition and said second condition in response to an application of a tensile force in said first direction, and wherein said crotch member is detachable from said body chassis member at said at least said portion of said attachment location in response to an application of a detaching shear force between said body chassis member and said crotch member in said first direction, wherein said tensile force is greater than said detaching shear force.

34. The disposable undergarment of claim 2 wherein each of said plurality of attachment locations extends longitudinally along a second direction substantially perpendicular to said first direction.

35. The disposable undergarment of claim 2 wherein said crotch member remains attached to said body chassis member at at least one of said plurality of attachment locations as said body chassis member is elongated between said relaxed and elongated conditions.

36. The method of claim 3 wherein said at least one of said plurality of attachment locations extends longitudinally along a second direction substantially perpendicular to said first direction.

* * * * *